(12) United States Patent
Liccardo et al.

(10) Patent No.: US 8,567,603 B2
(45) Date of Patent: *Oct. 29, 2013

(54) IMPLANT PACKAGE

(75) Inventors: Katherine Liccardo, Morris Plains, NJ (US); Delphine Patterson, East Rutherford, NJ (US); Joseph Wilmot, Rathkeale (IE); Sarah Grare, Washington, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/438,302

(22) Filed: Apr. 3, 2012

(65) Prior Publication Data

US 2012/0191203 A1    Jul. 26, 2012

Related U.S. Application Data

(63) Continuation of application No. 12/655,369, filed on Dec. 29, 2009.

(51) Int. Cl.
*A61B 17/06* (2006.01)

(52) U.S. Cl.
USPC .......................................................... 206/438

(58) Field of Classification Search
USPC .......... 203/438, 439, 363, 370; 206/438, 467, 206/469, 470, 471
See application file for complete search history.

(56) References Cited

U.S. PATENT DOCUMENTS

| | | | |
|---|---|---|---|
| 3,731,792 A * | 5/1973 | Rolston | 206/389 |
| 4,149,650 A * | 4/1979 | Whelchel et al. | 220/201 |
| 4,205,750 A * | 6/1980 | Dews | 206/534 |
| 4,597,765 A | 7/1986 | Klatt | |
| 4,697,703 A | 10/1987 | Will | |
| 4,750,619 A | 6/1988 | Cohen et al. | |
| 5,178,267 A | 1/1993 | Grabenkort et al. | |
| 5,193,679 A | 3/1993 | White | |
| 5,257,692 A | 11/1993 | Heacox | |
| 5,379,895 A | 1/1995 | Foslien | |
| 5,405,005 A | 4/1995 | White | |
| 5,568,865 A | 10/1996 | Mase et al. | |
| 5,664,408 A | 9/1997 | Chesterfield et al. | |
| 5,690,226 A | 11/1997 | N'Guyen | |
| 5,720,391 A | 2/1998 | Dohm et al. | |
| 5,868,253 A | 2/1999 | Krueger et al. | |
| 6,039,183 A | 3/2000 | Rudnick et al. | |
| 6,161,695 A | 12/2000 | Nicolais | |
| 6,622,864 B1 | 9/2003 | Debbs et al. | |
| 6,830,149 B2 | 12/2004 | Merboth et al. | |
| 6,863,692 B2 | 3/2005 | Meulink | |
| 2002/0029981 A1 | 3/2002 | Nigam | |
| 2003/0033016 A1 | 2/2003 | Dees | |
| 2003/0070944 A1 | 4/2003 | Nigam | |
| 2003/0213717 A1* | 11/2003 | Kanai | 206/495 |
| 2006/0213803 A1* | 9/2006 | Saitou et al. | 206/583 |
| 2007/0034538 A1 | 2/2007 | Landis | |
| 2011/0155592 A1 | 6/2011 | Liccardo et al. | |

* cited by examiner

*Primary Examiner* — Jacob K Ackun
(74) *Attorney, Agent, or Firm* — Lerner, David, Littenberg, Krumholz & Mentlik, LLP

(57) ABSTRACT

A system for packaging a medical implant may include a sleeve for housing the implant within a cavity in the sleeve, with at least a portion of the cavity conforming to the shape of the implant. A flexible material film may cover and substantially conform to the shape of the sleeve so as to aid in stabilizing the sleeve and implant within an outer package. An insertion instrument for inserting the implant within the body of a patient may also be provided with the system. In some embodiments, the sleeve, with the implant inserted in the cavity of the sleeve, is configured for manipulation by a user without contacting the implant, and the implant is connectable to the insertion instrument while in the sleeve.

10 Claims, 9 Drawing Sheets

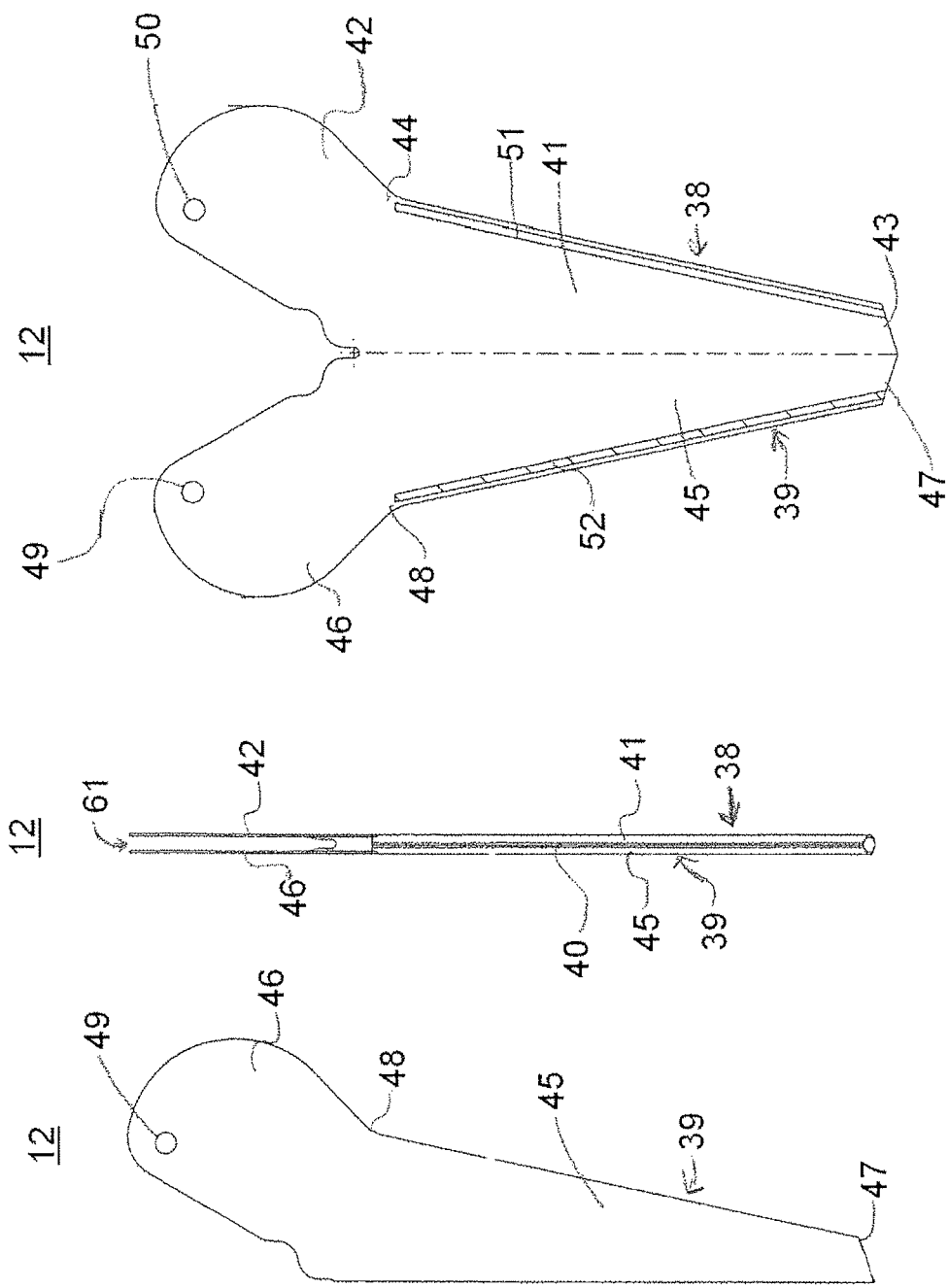

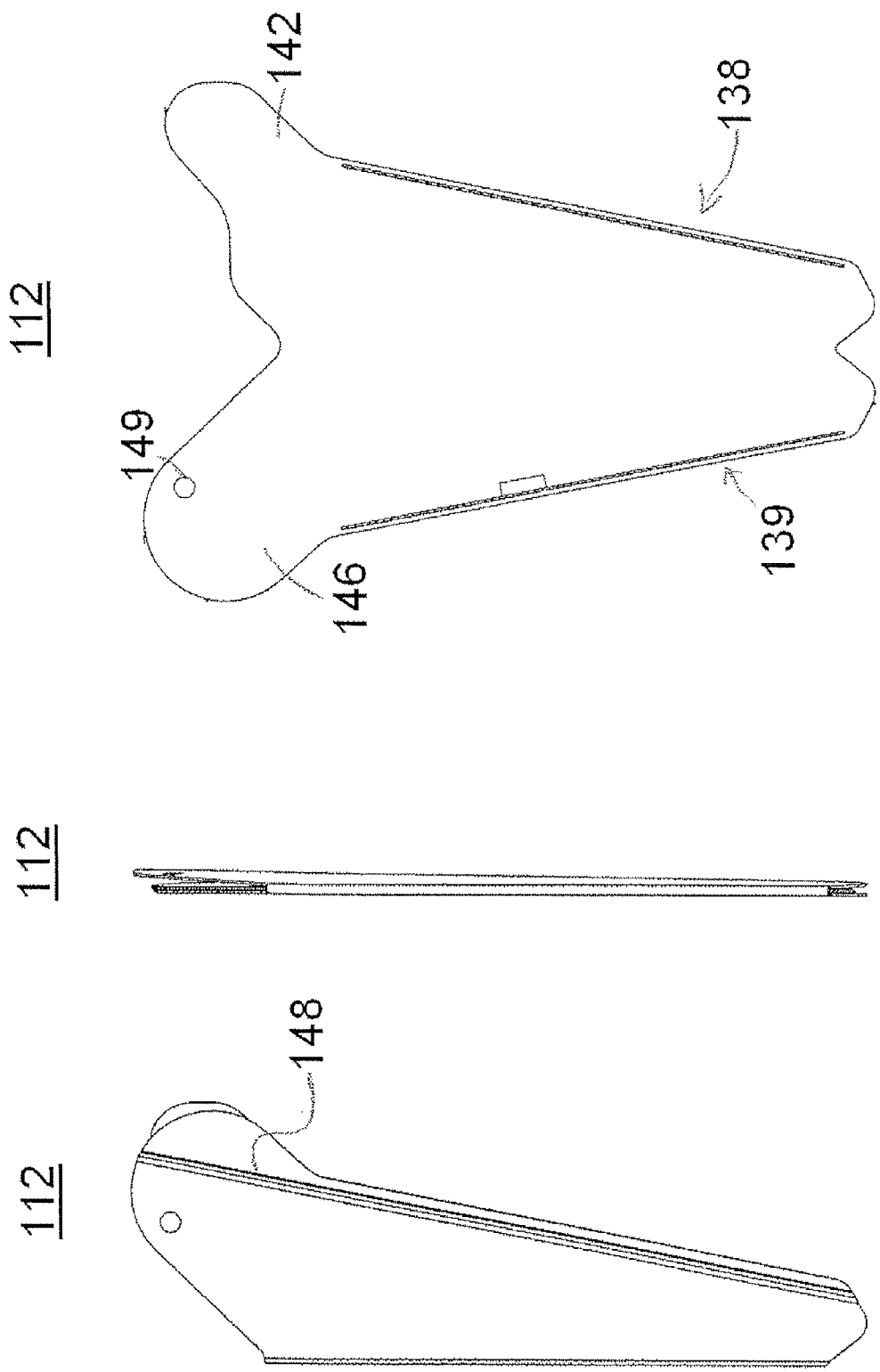

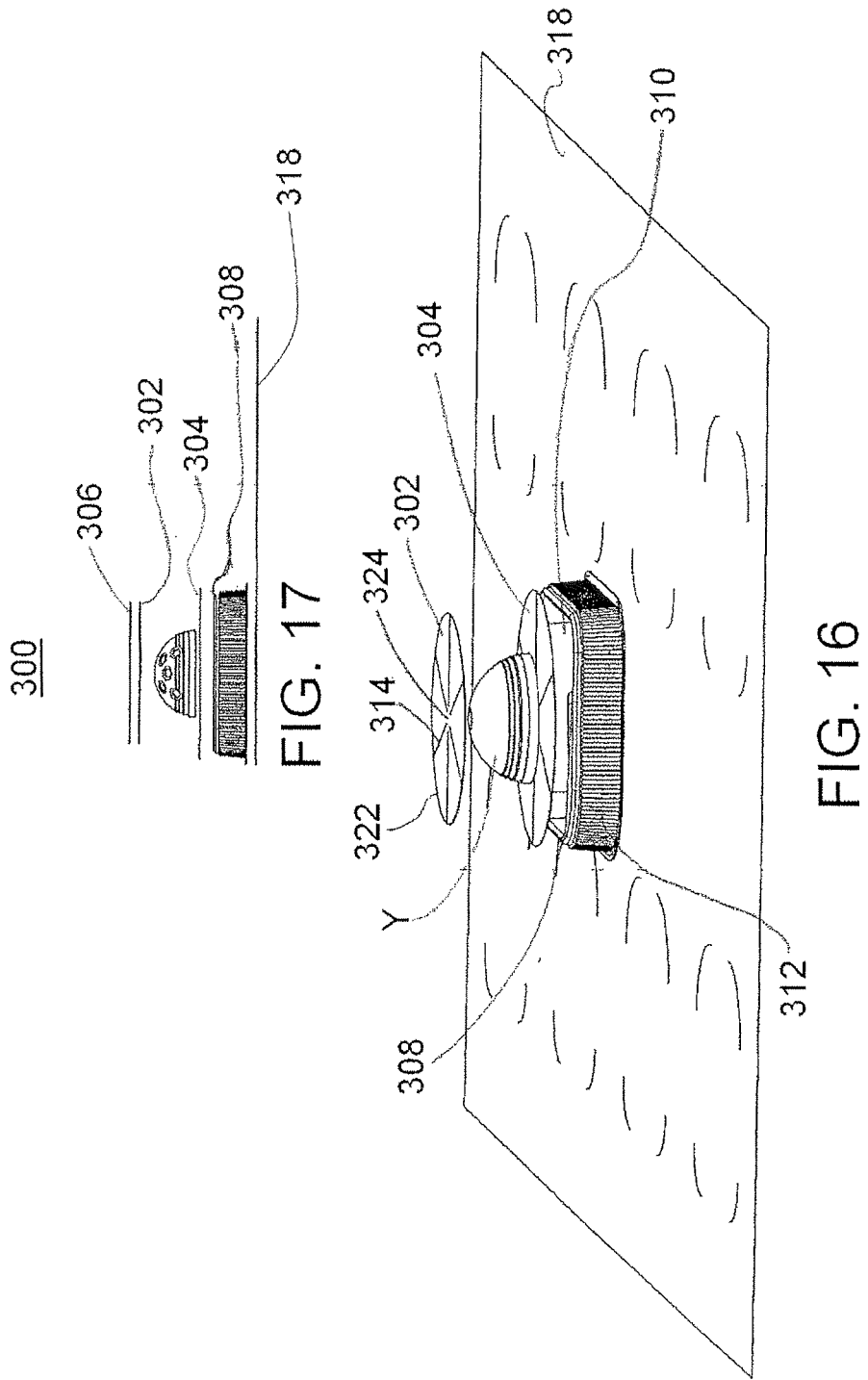

IMPLANT PACKAGE

CROSS-REFERENCE TO RELATED APPLICATIONS

The present application is a continuation of U.S. patent application Ser. No. 12/655,369, filed Dec. 29, 2009, the disclosure of which is incorporated herein by reference.

BACKGROUND OF THE INVENTION

The present disclosure relates to apparatuses and methods for packaging a medical device. More specifically, the present disclosure relates to packages for holding a medical implant and processes for making said packages.

Conventional implant packages rely on a void-filling approach to protect their contents. The void-filling approach entails stabilizing the contents within a rigid plastic package with a variety of foams and padding materials. The foam and padding materials essentially fill the void between the implant and the inner surfaces of the rigid plastic package. The rigid plastic package is then sealed with lidstock material.

The void-filling approach requires the use of multiple foam components. These components are usually bulky and generate a considerable volume of package waste. Additionally, implants packed in foam can be difficult to remove without premature or accidental exposure to biological material on surgical gloves since the foams are intended to provide a tight fit to cushion the package and the implant. The void-filling approach also requires some manual processes, which are prone to error and typically result in a long packaging process time.

Packages filled with foam also experience problems during transportation. As a package is transported, the foam contained within the package may compress due to the repeated motion experienced during shipping. As a consequence, heavy implants packed in foam must be packed very tightly. Compressed foam allows more implant motion within the package. This implant motion may damage the implant and/or the package and negate the sterile barrier. Once the sterile barrier of a package has been compromised, the medical implant contained within that package cannot be used in surgery. What's more, if a medical implant has been contaminated and the physician has no back-up medical implant on hand, surgery could be delayed.

Foams used in void-filling packages may jeopardize the sterility of the medical implants in other ways. For instance, friction between the foam and the medical implant can abrade the foam and generate particulate. Moreover, when the medical implant is packed tightly with foam to reduce implant motion, the foam may occasionally adhere to the package lidstock during the sealing process. As a result of this improper adhesion, the foam may scorch or shear apart when the package is opened by the end user. Both of these situations may endanger the implant sterility. If the implant has been contaminated and no back-up implant is readily available, surgery could be delayed.

Although implant packages like the void-filled implants packages are well known in the art, improvements are always possible.

BRIEF SUMMARY OF THE INVENTION

The present disclosure relates to a packaging assembly for holding a medical implant. An embodiment of the presently disclosed packaging assembly includes a substantially rigid base having a cavity dimensioned to receive a medical implant, a sleeve positioned within the cavity of the substantially rigid base and defining an opening dimensioned to receive the medical implant, and a skin pack material sealed to the lid stock and collar to enclose and secure the sleeve in the cavity of the substantially rigid base. The sleeve has a shape substantially similar to a shape of the medical implant and substantially envelopes the medical implant when the medical implant is positioned in the opening of the sleeve. The skin pack lid has a geometry that substantially conforms to the shape of the sleeve.

In another embodiment, the presently disclosed packaging assembly includes a substantially rigid base having a cavity dimensioned to receive a medical implant, a flexible pad positioned in the cavity of the substantially rigid base, a flexible cover placed over the outer surface of the medical implant, and a skin pack material sealed to the lid stock and collar to enclose and secure the medical implant enveloped by the flexible pad and the flexible cover within the cavity of the substantially rigid base. The flexible pad engages at least a portion of the lower or bottom surface of the medical implant. The flexible cover has a shape that substantially conforms to the shape of the outer surface of the medical implant. The skin pack lid has a geometry that substantially conforms to the shape of the medical implant.

The present disclosure further relates to a method of packaging a medical implant. In one embodiment, this method includes the steps of inserting a medical implant inside a sleeve, placing the sleeve with the medical implant on a substantially rigid base, and sealing a skin film over the substantially rigid base using a skin packing process.

The present disclosure further relates to another method of packing a medical implant, which includes the steps of wrapping a medical implant with a flexible cover and a flexible pad, placing the wrapped medical implant on a substantially rigid base, and sealing a flexible film over the substantially rigid base using a skin packing process.

BRIEF DESCRIPTION OF THE DRAWINGS

Various embodiments of the presently disclosed packaging assembly are disclosed herein with reference to the drawings, wherein:

FIG. 7 is a top view of an embodiment of a sleeve for use with the package shown in FIG. 1 in a sealed position;

FIG. 8 is a side elevation view of the sealed sleeve depicted in FIG. 7;

FIG. 9 is a side elevation view of the sleeve of FIG. 7 in an unsealed position;

FIG. 10 is a top view of an embodiment of a sleeve for use with the package shown in FIG. 1 in a sealed position;

FIG. 11 is a side elevation view of the sealed sleeve illustrated in FIG. 10;

FIG. 12 is a top view of the sleeve of FIG. 10 in an unsealed position;

FIG. 16 is an isometric exploded view of an alternate embodiment of a package for use with an acetabular cup;

FIG. 17 is a side exploded view of the package shown in FIG. 16; and

DETAILED DESCRIPTION

Figure 1:
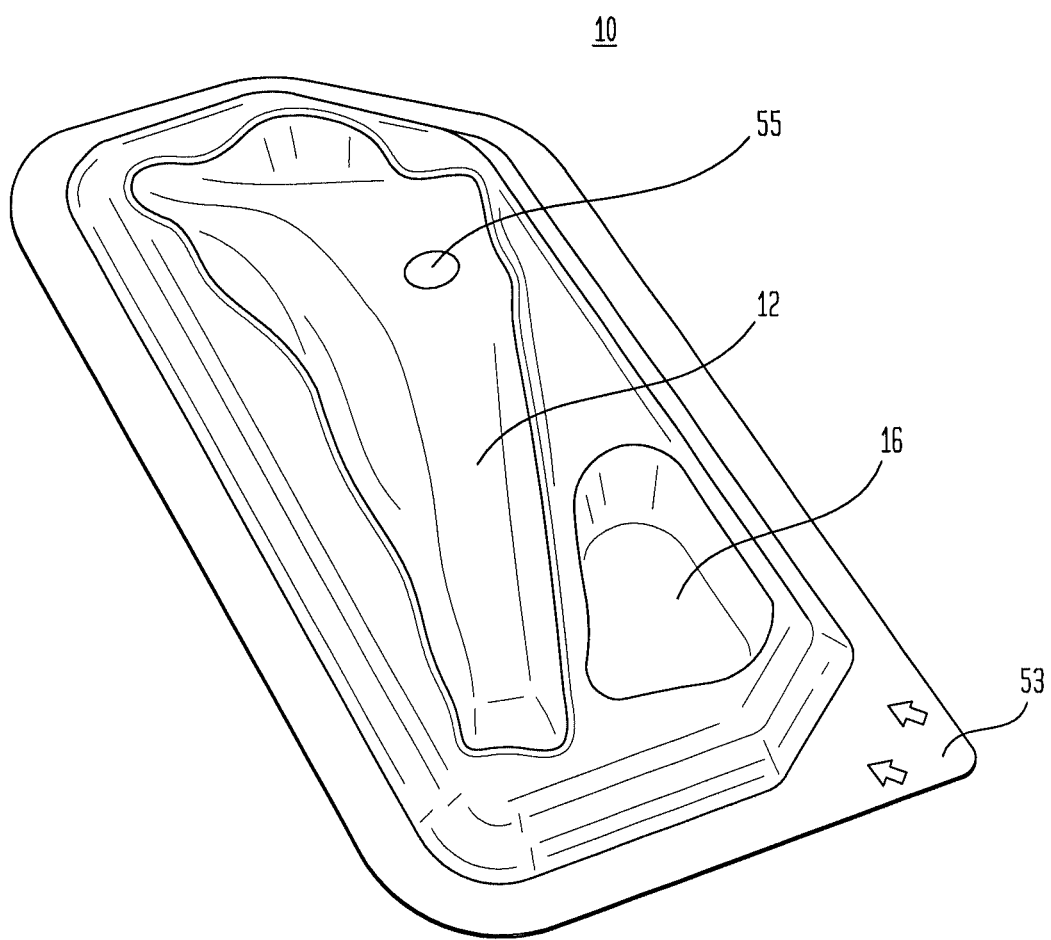
FIG. 1 is an isometric view of a package in accordance with an embodiment of the present disclosure.
Figure 2:
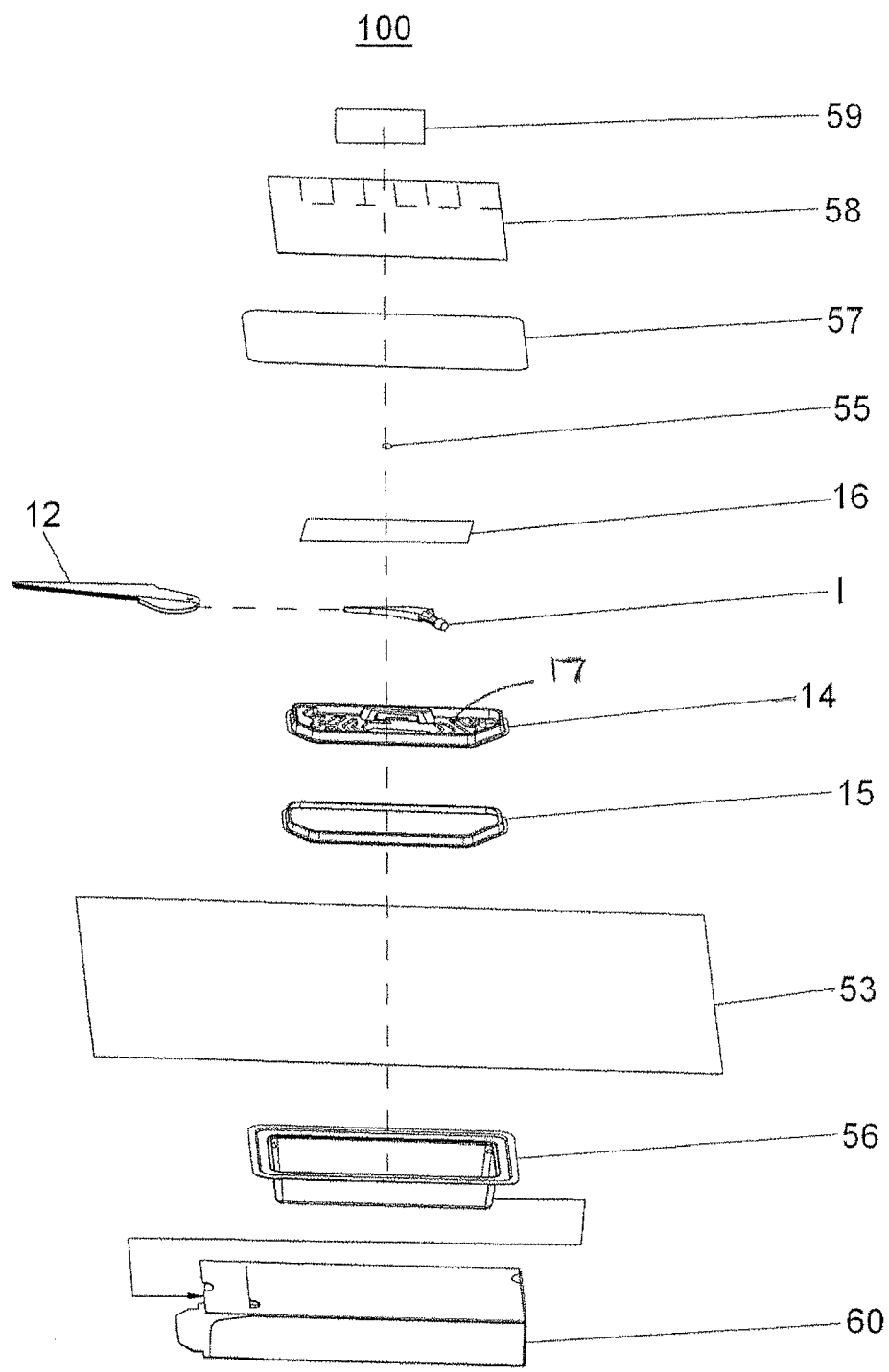
FIG. 2 is an isometric exploded view of the packaging assembly, which includes the package shown in FIG. 1.

With reference to FIGS. 1 and 2, the present disclosure relates to a package 10 for holding any suitable medical item such as an orthopaedic medical implant I. Package 10 is part of a packaging assembly 100 and generally includes a sleeve 12, a substantially rigid base or tray 14, a skin pack film or lid 16, and a collar 15. Base 14 defines a cavity 17 and may be wholly or partly made of a rigid polymer. Cavity 17 is dimensioned to receive medical implant I contained inside sleeve 12. Sleeve 12 defines an opening 61 (see FIG. 8) extending therethrough and prevents, or at least hinders, skin pack lid 16 from wrapping medical implant I too tightly. Opening 61 of sleeve 12 is adapted to receive medical implant I. In some embodiments, sleeve 12 is wholly or partly made of glycol-modified polyethylene terephthalate ("PETG") or any other suitable thermoplastic. In certain embodiments, the shape of sleeve 12 is substantially similar to the shape of medical implant I. Consequently, when medical implant I is positioned inside sleeve 12, sleeve 12 substantially envelopes medical implant I. During assembly, a sleeve 12 containing medical implant I is positioned within cavity 17 of base 14. Skin pack lid 16 is sealed over collar 15 and base 14 to enclose and secure sleeve 12 inside cavity 17. Skin pack lid 16 is then vacuum formed over sleeve 12. As a consequence, skin pack lid 16 attains a geometry that substantially conforms to the shape of sleeve 12. Although skin pack lid 16 is sealed over base 14, skin pack lid 16 is actually adhered to collar 15, which surrounds a periphery of base 14.

Figure 3:
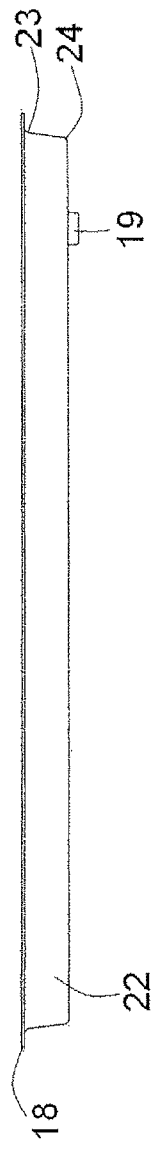
FIG. 3 is a side elevation view of a base of the package depicted in FIG. 1.
Figure 4:
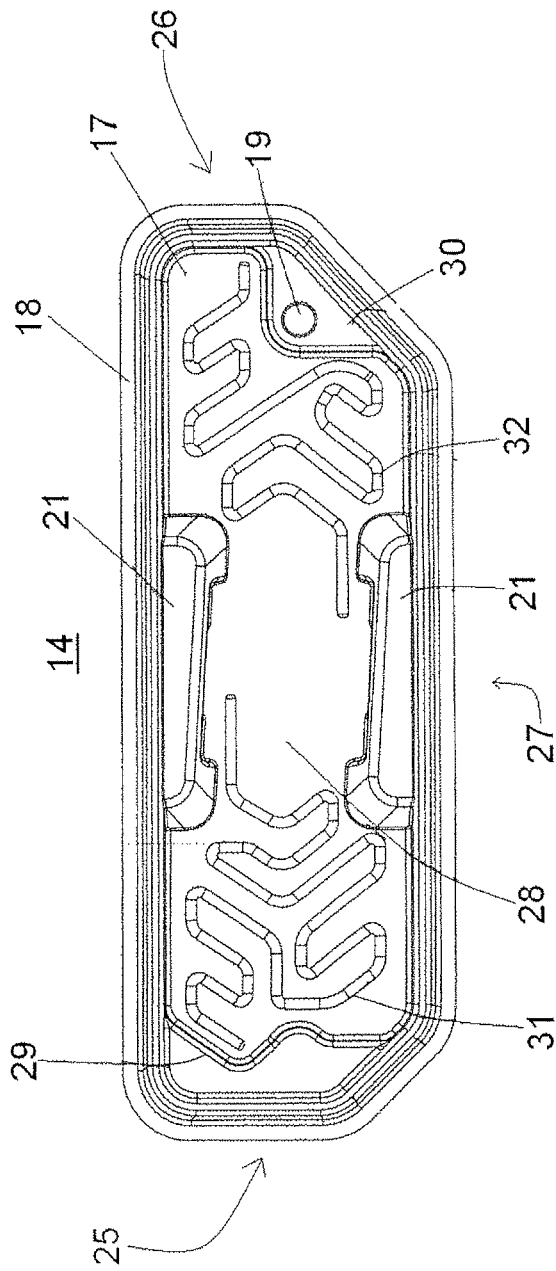
FIG. 4 is a top view of the base illustrated in FIG. 3.

Referring to FIGS. 3 and 4, base 14 has a first end portion 25, a second end portion 26, and a central portion 27 located between first and second end portions 25, 26 and incorporates an exterior wall 22, a cavity 17 located within the confines of exterior wall 22, a rim 18 surrounding a periphery of the base 14, a supporting surface 28 for supporting sleeve 12, and means for retaining or locating sleeve 12 relative to base 14, as discussed in detail below. Exterior wall 22 encloses cavity 17 and includes a first end 23 and a second end 24. In some embodiments, exterior wall 22 has six sides joined by six rounded corners. In other embodiments, exterior wall has a substantially oblong shape. However, exterior wall 22 may have any suitable shape or configuration. Rim 18 is positioned around first end 23 of exterior wall 22 and extends outwardly from exterior wall 22. Supporting surface 28 is oriented substantially parallel to rim 18 and is located adjacent to first end 23 of exterior wall 22. In use, sleeve 12 (FIG. 2) is placed on supporting surface 28. Sleeve 12 is in turn secured to base 14 by any suitable structure or means, as will be discussed below.

In some embodiments, the means for retaining or locating sleeve 12 relative to base 14 includes first and second inner walls 29, 30 extending from supporting surface 28. First inner wall 29 is located adjacent to first end portion 25 of base 14, whereas second inner wall 30 is positioned adjacent to second end portion 26 of base 14. When sleeve 17 is placed on supporting surface 28, first and second inner walls 29, 30 limit the motion of sleeve 12 during shipping of package 10.

The means for retaining or locating sleeve 12 relative to base 14 may (additionally or alternatively) include a pin 19 for engaging one or more holes in sleeve 12 (see e.g., holes 49 and 50 in FIG. 9). In some embodiments, pin 19 extends from second inner wall 30 past beyond second end 24 of exterior wall 22, as seen in FIG. 3. As discussed in detail below, sleeve 12 has a hole dimensioned to securely receive pin 19. When pin 19 engages the hole of sleeve 12, sleeve 12 is secured to base 14, thereby maintaining the location of sleeve 12 with respect to cavity 17.

Moreover, the means for retaining or locating sleeve 12 relative to base 14 may (additionally or alternatively) include at least one ridge (31 or 32) formed on supporting surface 28. In the embodiment depicted in FIG. 4, base 14 includes first and second ridges 31, 32 for increasing the friction between sleeve 12 and supporting surface 28 when sleeve 12 is placed in base 14. First ridge 31 has a twisted configuration and extends from a location adjacent to first inner wall 29 to central portion 27 of base 14. Second ridge 32 also has a twisted configuration and extends from second end portion 26 of base 14 toward central portion 27 of base 14. At least a portion of second ridge 32 is located adjacent to second inner wall 30.

In certain embodiments, base 14 incorporates at least one rib 21 for limiting the movement of sleeve 12 inside cavity 17. In the embodiment shown in FIG. 4, base 14 includes two ribs 21 formed on supporting surface 28 at central portion 27 of base 14. Although both ribs 21 are positioned in central portion 27, ribs 21 are located on opposite sides of external wall 22. On the side of supporting surface 28 facing cavity 17, both ribs 21 have a raised profile configured to engage sleeve 12. On the side of supporting surface 28 facing away from cavity 17, each rib 21 defines a void adapted to receive a user's fingers. In use, the end user can place the fingers in these voids to grab base 14 and then separate base 14 from skin pack lid 16.

Figure 5:
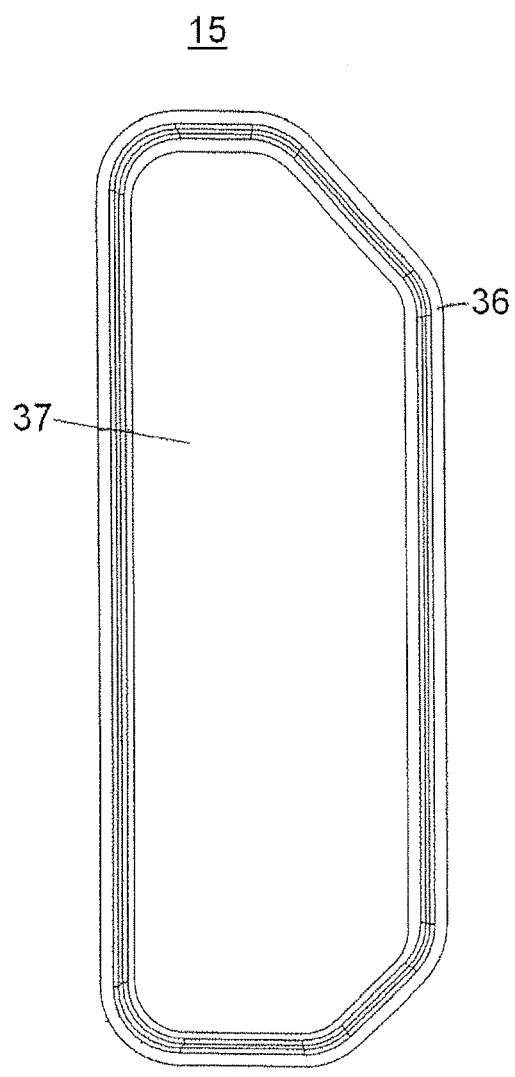
FIG. 5 is a top view of a collar of the package shown in FIG. 1.
Figure 6:
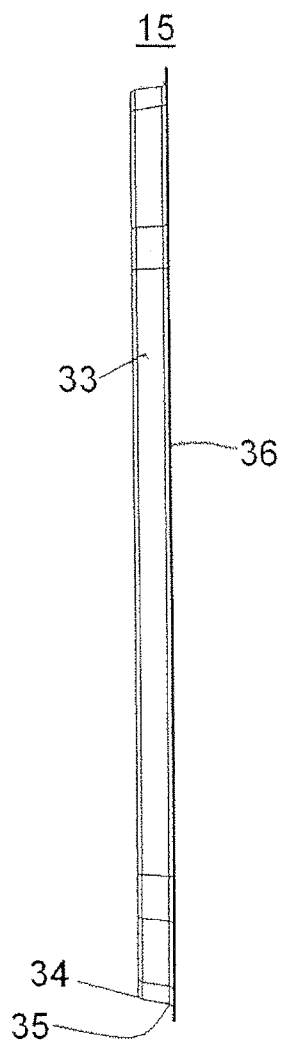
FIG. 6 is a side elevation view of the collar depicted in FIG. 5.

With reference to FIGS. 5 and 6, package 10 further includes a collar 15 configured to be positioned around a periphery of base 14. Collar 15 defines a central opening 37 and includes an exterior wall 33 surrounding central opening 37. Central opening is configured to receive base 14. External wall 33 includes a first end 34 and a second end 35 and has a shape substantially similar to the shape of exterior wall 22 of base 14. Consequently, collar 15 is adapted to form around a periphery of base 14. A flange 36 extends outwardly from second end 35 of external wall 33. Flange 36 has a generally planar shape. In several embodiments, collar 15 has six sides joined by six rounded corners. Collar 15, however, may have any suitable shape or configuration so long as it fits around the periphery of base 14. When package 10 is assembled, skin pack film or lid 16 is adhered to flange 36 of collar 15 rather than base 14. As a result, an end user can separate base 14 from skin pack film or lid 16 without cutting package 10.

FIGS. 7-9 show an embodiment of sleeve 12. This embodiment of sleeve 12 includes first and second sides 38, 39 coupled to each other and is made wholly or partly of a biocompatible flexible material. In one embodiment, sleeve 12 is made wholly or partly of a biocompatible polyurethane. The precise shape of sleeve 12 depends on the implant to be packed inside said sleeve 12. For example, sleeve 12 can be designed to accommodate hip femoral implants, shoulder humeral implants, and other implants with a general oblong shape. In any event, sleeve has a shape substantially similar to the shape of medical implant I or any other suitable implant.

In the embodiment shown in FIGS. 7-9, first and second sides 38, 39 have substantially similar shapes. First side 38 can be bent and sealed over second side 39 and vice-versa. In some embodiments, a living hinge 40 or any suitable structure or means connects first side 38 to second side 39. In these embodiments, first side 38 can be bent over second side 39 along living hinge 40. First side 38 includes an elongate portion 41 having a substantially triangular shape and a flange 42 extending from elongate portion 41. Elongate portion 41 of first side 38 has a first end 43 and a second end 44 and includes a sealing area 51 extending between first and second ends 43, 44. In use, elongate portion 41 covers an elongate portion of medical implant I, such as the stem of a hip femoral implant. First and second sides 38, 39 may be heat sealed along sealing areas 51, 52, which are located along the borders of elongate portions 41, 45. Flange 42 is connected to second end 44 of elongate portion 41 and has a hole 50 adapted to securely receive pin 19 (FIG. 4) of base 14. The secure engagement between pin 19 and hole 50 helps limit the motion of sleeve 12 within cavity 17 of base 14. At least a portion of flange 42 has a rounded profile. The rounded profile of flange 42 assists in covering rounded features of medical implant I.

Second side 39 also has an elongate portion 45 having a substantially triangular shape and a flange 46 extending from elongate portion 45. Elongate portion 45 has a first end 47 and a second end 48 and includes a sealing area 52 extending between first and second ends 47, 48. Sealing area 52 is positioned along a border of elongate portion 45. As discussed above, the first and second sides 38, 39 may be heat sealed along sealing areas 51, 52 when first and second sides 38, 39 are bent over each other. Flange 46 is connected to second end 48 of elongate portion 45 and has a hole 49 adapted to securely receive pin 19 of base 14. The secure engagement between pin 19 and hole 49 helps hinder the motion of sleeve 12 within cavity 17 of base 14. Hole 49 is substantially aligned with hole 50 of first side 38 when first side 38 is bent over second side 39. At least a section of flange 46 has a rounded profile, which assists in covering rounded features of medical implant I.

When first side 38 is bent over second side 39, sleeve 12 defines an opening 61 extending therethrough. Opening 61 is sized to receive medical implant I. When medical implant I is positioned in opening 61 of a sealed sleeve 12, elongate portions 41, 45 of first and second sides 38, 39 can collectively envelop a portion of medical implant I, such as a stem of a hip femoral implant, and flanges 42, 46 can together enclose a portion of medical implant I, such as the cup and ball of a hip femoral implant.

Referring to FIGS. 10-12, another embodiment of the sleeve is generally designated with reference number 112. The structure and operation of sleeve 112 are similar to the structure and operation of sleeve 12. However, the shape of flange 142 of first side 138 is different from the shape of flange 146 of second side 139. In addition, flange 146 of second side 139 has a hole 149 adapted to securely receive pin 19 of base 14, while flange 142 of first side 138 does not have a hole. Moreover, flange 146 is larger than flange 142. Second side 139 further includes another bendable axis or ridge 148 formed on its outer surface. Ridge 148 extends along the entire length of the second side 139.

Figure 15:
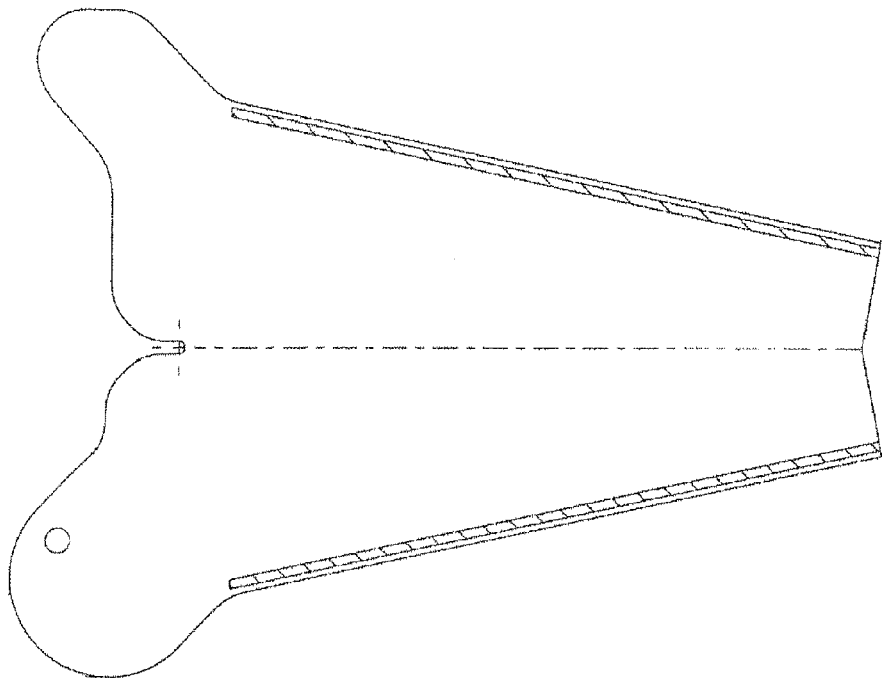
FIG. 15 is a top view of the sleeve of FIG. 13 in an unsealed position.
Figure 14:
FIG. 14 is a side elevation view of the sealed sleeve illustrated in FIG. 13.
Figure 13:
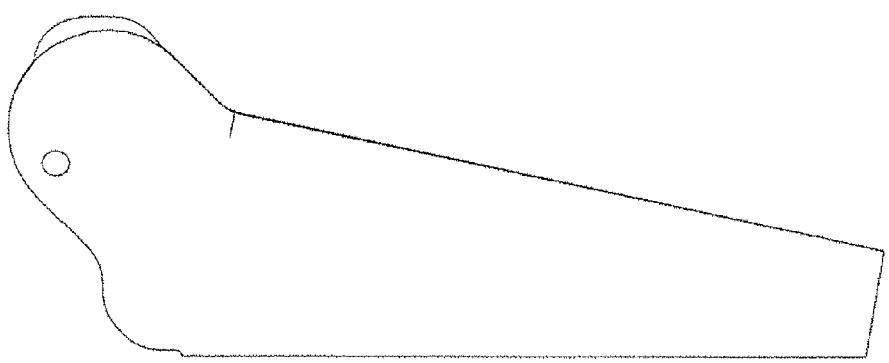
FIG. 13 is a top view of an embodiment of a sleeve for use with the package shown in FIG. 1 in a sealed position.

FIGS. 13-15 illustrate another embodiment of sleeve 212. Sleeve 212 is substantially similar to sleeve 112 but does not include ridge 148.

Returning to FIGS. 1 and 2, during assembly, a skin packing machine is loaded with a roll or sheet of lidstock 53 and a roll of flexible seal material, which eventually turns into skin pack lid 16. In an exemplary method, the manufacturers utilize an ASP Series skin packing machine sold by Starview Packaging Machinery, Inc. under the trademark STARVIEW. Lidstock 53 is made of any suitable medical grade packaging material. In one embodiment, lidstock 53 is made of the nonwoven material comprising of spunbond olefin fiber, which is sold by DUPONT under the trademark TYVEK. Base 14 is placed on a sheet of lidstock material 53 in a designated location. Medical implant I is inserted inside opening 61 of a sealed sleeve (12, 112, or 212). Alternatively, medical implant I is placed on one side (e.g., 38 or 39) of sleeve 12 (or any other sleeve described above) and then one side is sealed over the other side of sleeve 12 to enclose medical implant I within sleeve 12. Once medical implant I has been enveloped by sleeve 12, sleeve 12 (along with medical implant I) is placed in cavity 17 of base 14. To secure sleeve 12 to base 14, pin 19 of base 14 can be introduced through holes (e.g., 49 and 50) of sleeve 12.

Before or after placing medical implant I inside base 308, collar 15 is positioned around base 308. Next, a piece of the flexible seal material is sealed over base 14 to form skin pack film or lid 16. In some embodiments, the flexible seal material is wholly or partly made of a resin. Regardless of the particular material employed, the flexible seal material is placed over base 14 and sealed to collar 14 using a skin packing process.

In one exemplary method, the skin packing process involves heating the flexible seal material to soften it. Once softened, the flexible film material can be stretched and placed over base 14 to cover the opening leading to cavity 17. The flexible seal material, however, is adhered to collar 15, which is positioned around base 14.

After placing the flexible film material over base 14, a manufacturer employs vacuum forming to shape the flexible seal material and, therefore, form skin pack film or lid 16. In one exemplary method, vacuum forming involves applying a vacuum between base 14 and the flexible seal material to mold the shape of the flexible seal material. As a result of this process, the flexible seal material forms a skin pack film or lid 16 having a geometry that substantially conforms to the shape of the sleeve 12 containing medical implant I.

Then, skin pack film or lid 16 is adhered to collar 15. Since skin pack lid 16 is adhered to collar 15 rather than base 14, an end user can separate base 14 from skin pack film or lid 16 without cutting package 10. Lidstock 53 is also adhered to collar 15.

Subsequently, a radiation or sterilization indicator 55 may be attached to an outer surface of skin pack lid 16. Indicator 55 has a signal response to sterile processing conditions experienced by medical implant I and includes an ink having color-change response to exposure to sterilization processing to signal a history of sterile processing. In some embodiments, the ink is responsive to exposure to radiation or a sterilizing gas such as ethylene oxide. In certain embodiments, the ink is responsive to sterilizing steam or vapor, or organic agents such as formaldehyde.

Following the assembly of package 10, package 10 is positioned in an outer blister or tray 56. Outer blister 56 is sealed with another lidstock 57. Like lidstock 53, lidstock 57 is made of any suitable medical grade packaging material. In one embodiment, lidstock 57 is made of the nonwoven material comprising of spunbond olefin fiber, which is sold by DUPONT under the trademark TYVEK.

A label 58 is then attached to the outer surface of lidstock 57. Once package 10 has been shipped to the end user, patient information may be printed on label 58. A package insert 59 may be attached to the outer surface of label 59. Usually, package insert 59 contains information required by regulatory agencies.

The sealed outer blister 56 is then placed inside a box 60. After closing box 60, shrink wrap may be applied over box 60 to protect its contents.

Figure 18:
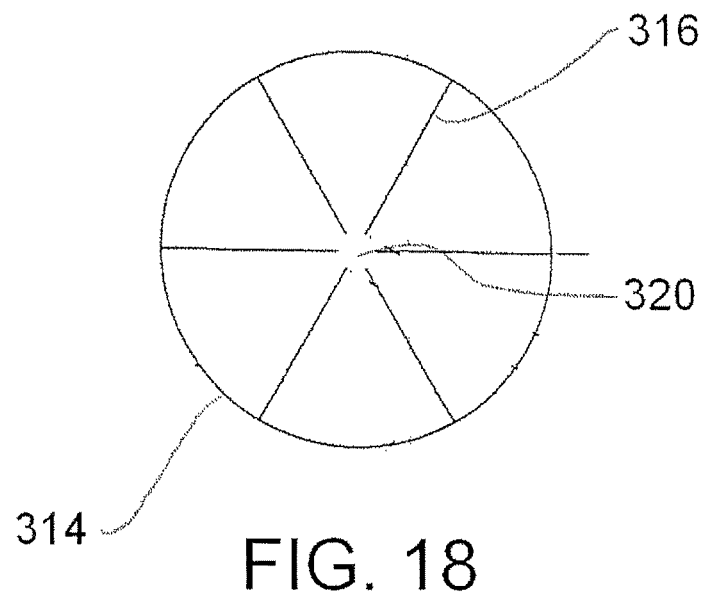
FIG. 18 is a top view of the lower flexible pad of the package shown in FIG. 16.

With reference to FIGS. 16-18, a package 300 is designed for holding generally hemispherical or spherical shaped implant Y. For illustration purposes only, the drawings shows a hip acetabular shell, but package 300 can retain many other kinds of implants such as knee femoral implants, knee tibial implants, hip acetabular heads, shoulder head implants, among others. Package 300 includes a base or tray 308, a flexible cover 302, a flexible pad 304, a collar 312, and a skin pack film or lid 306.

Base 308 is made wholly or partly of a substantially rigid material, such as a rigid plastic, and has a cavity 310 dimensioned to receive medical implant Y. One side of base 308 has a supporting surface adapted to support medical implant Y, and another side of base 308 has an opening leading to cavity 310.

A collar 312 is positioned around the periphery of base 308. Specifically, collar 312 surrounds an external wall of base 308. Accordingly, the shape of collar 312 is substantially similar to the shape of the external wall of base 308.

Package 300 may additionally include a structure or means for securing medical implant Y (along with flexible pad 304 and flexible cover 302) to base 308. This means or structure may be substantially similar to the means for securing sleeve 12 to base 14 described above.

During assembly, a skin pack film or lid 306 is sealed over base 308 and adhered to collar 312 after positioning medical implant I, flexible pad 304, and flexible cover 302 inside cavity 310. Flexible pad 304 and flexible cover 302 prevent, or at least inhibit, skin pack lid 306 from wrapping medical implant Y too tightly, preventing easy removal of medical implant Y. This arrangement allows the end user to separate skin pack film or lid 306 from base 308 without cutting package 300.

As seen in FIG. 18, flexible pad 304 includes at least one slit 326 extending from an exterior edge 314 to a central portion 320 thereof. Slit 326 enhances the flexibility of flexible pad 304. In the depicted embodiment, flexible pad 304 features a circular shape and has six slits 326 spread around its superficial area. Nonetheless, flexible pad 304 may have any other suitable shape and may include more or fewer slits 326. Irrespective of the specific number of slits 326, flexible pad 304 is configured to wrap an inner surface of medical implant Y.

Flexible cover 302 is substantially similar to flexible pad 304 but may have a different size than flexible pad 304, as shown in FIGS. 16 and 17. In the depicted embodiment, flexible cover 302 is smaller than flexible pad 304. The sizes of flexible cover 302 and flexible pad 304 would ultimately depend on the medical implant Y to be packed. Flexible cover 302 also has at least one slit 326 for enhancing its flexibility. Slit 326 extends from an outer edge 322 to a central portion 324 of flexible cover 302. While FIG. 16 shows flexible cover 302 with six slits 326 and featuring a circular superficial area, flexible cover 302 may include more or fewer slits 326 and may have other suitable shapes and configurations. In any case, flexible cover 302 is configured to wrap an external surface of medical implant Y.

It is envisioned that flexible cover 302 and flexible pad 304 can be monolithically formed. Alternatively, flexible cover 302 and flexible pad 304 can be separate components. In any event, flexible cover 302 and flexible pad 304 collectively wrap around medical implant Y and maintain a sterile barrier around medical implant Y.

During assembly, a skin packing machine is loaded with a roll of lidstock 318 and a roll of flexible seal material. Lidstock 318 is made of any suitable medical grade packaging material. In one embodiment, lidstock 318 is made of the nonwoven material comprising of spunbond olefin fiber sold by DUPONT under the trademark TYVEK. Base 308 is placed on a sheet of lidstock material 318 in a designated location. Medical implant Y is centered on flexible pad 304. Then, the shape of flexible pad 304 is substantially conformed to the shape of an inner surface of medical implant Y. At this point, flexible pad 304 covers (entirely or substantially) the inner surface of medical implant Y. Flexible cover 302 is subsequently placed over medical implant Y to cover (entirely or substantially) the outer surface of medical implant Y. Once medical implant Y has been enveloped by flexible cover 302 and flexible pad 304, medical implant Y (along with flexible cover 302 and flexible pad 304) is placed in cavity 310 of base 308, with flexible pad 304 abutting the supporting surface of base 308.

Before or after placing medical implant Y inside base 308, collar 312 is positioned around base 308. Next, a flexible seal material is sealed over base 308 to form skin pack film or lid 306. In some embodiments, the flexible seal material is made of resin. Regardless of the particular material employed, the flexible seal material is sealed over base 308 and adhered to collar 312 using a skin packing process.

In one exemplary method, the skin packing process involves heating the flexible seal material to soften it. Once softened, the flexible seal material can be stretched and placed over base 308 to cover the opening leading to cavity 310 of base 308. The flexible seal material, however, is adhered to collar 312, which is positioned around base 308.

After placing the flexible seal material over base 308, a manufacturer employs vacuum forming to shape the flexible seal material and, therefore, form skin pack film or lid 306. In one exemplary method, vacuum forming involves applying a vacuum between base 308 and the flexible seal material to mold the shape of the flexible seal material. As a result of this process, the flexible seal material forms a skin pack film or lid 306 having a geometry that substantially conforms to the shape of the medical implant Y enveloped by flexible pad 304 and flexible cover 302.

Then, skin pack film or lid 306 is adhered to collar 312. Since skin pack film or lid 306 is attached to collar 312 rather than base 308, an end user can separate base 308 from skin pack film or lid 306 without cutting package 300. Lidstock 318 is also adhered to collar 312. Package 300 can also be contained in outer blister 56 and the packed in box 60.

In use, an end user may remove the implant from package (10 or 300) without contacting the implant surfaces. First, the user opens box 60 and removes outer blister 56 from box 60. Then, the user peels back lidstock 57 from outer blister 56 to access package 10 or 300.

To remove the implant from either package 10 or 300, the end user peels back sheet of lidstock 23 or 318 adhered to collar 15 or 312. Subsequently, the end user separates base 14 or 308 from skin pack lid 16 or 306. While separating base 14 or 308 from skin pack lid 16 or 306, the end user should maintain a gentle grip on the implant through sleeve 12 or cover 302. Then, the end user removes the implant from package (10 or 300). During removal and afterwards, the end user grabs the implant through sleeve 12 or cover 302 and pad 304, without contacting the implant surface. No tool is required to remove the implant from the package (10 or 300).

Once the end user has removed the implant from package (10 or 300), an insertion instrument can be attached to the implant without removing the implant from sleeve 12 or cover 302 and pad 304.

The processes described above results in substantially advantages over other known packaging processes. In particular, the use of sleeve 12 or cover 302 in conjunction with skin packaging greatly reduces the volume of package waste generated when an implant is consumed. Fewer components are required to package the implants, and the implant can be packed in multiples. Sleeve 12 allows the end user to grasp the sterile implant firmly without contacting the implant surface. Instruments required to place the implant in a patient body can be attached while the implant is being held by sleeve 12, reducing the risk of premature contact with fluids. In addition, the skin package eliminates, or at least minimizes, motion within the packages (10 or 300). Neither sleeve 12 nor cover 302 and pad 304 substantially compress the implant, keeping the implant firmly positioned until opened by the end user.

Moreover, sleeve 12 or cover 302 and pad 304 protect implant coatings and surface finish from damage. In turn, skin pack lid (16 or 306) is protected from implant coatings and sharp features. Additionally, sleeve 12 and cover 302 allow the end user to handle the implant without actually contacting the implant surface. Sleeve 12 and cover 302 also provide packages (10 or 300) with sleeker inner package profiles as compared with other implant packages.

Further, the skin packing process described above results in substantial cost savings. Since the presently disclosed skin packaging processes do not entail the use of foams, the manufacturer may save time by using sleeves 12 or covers 302 and pads 304, as opposed to foams. For example, the void-filling packaging approach, which entails the use of foam, typically requires manual packing. The use of sleeves 12 or covers 302 and pads 304 in a skin packing process, on the other hand, can be performed automatically by machines. Thus, the skin packing process allows the manufacturer to package the medical implant quicker than if foams were employed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for packaging a medical implant comprising:
   an implant;
   a sleeve housing the implant within a cavity in the sleeve, at least a portion of the cavity conforming to the shape of the implant;
   a flexible material film covering and substantially conforming to the shape of the sleeve; and
   an insertion instrument for inserting the implant within the body of a patient, the insertion instrument being connectable to the implant while housed in the sleeve,
   wherein the sleeve, with the implant inserted in the cavity of the sleeve, is configured for manipulation by a user without contacting the implant.

2. The system of claim 1, wherein the flexible material film is vacuum formed over the sleeve to aid in stabilizing the sleeve and implant when inserted into an outer package.

3. The system of claim 1, wherein the sleeve further comprises a first side having outer and inner surfaces and a perimeter, and a second side having outer and inner surfaces and a perimeter, the first and second sides being connected at least along portions of their respective perimeters to form the cavity and situate the inner surfaces of the first and second sides adjacent one another.

4. The system of claim 3, wherein the first and second sides, in combination, cover at least a portion of the medical implant while leaving a remainder of the implant exposed so that the sleeve may be grasped by a user without contacting the implant.

5. The system of claim 4, wherein the exposed portion of the implant is connectable with the insertion instrument.

6. A packaging system for holding a medical implant comprising:
   an implant;
   a sleeve including:
      a cavity for housing the implant; and
      a first side and a second side, wherein the second side is joined to the first side to conform a portion of the sleeve to the shape of the implant; and
   a flexible material film covering and substantially conforming to the shape of the sleeve,
   wherein, in one configuration, a first portion of the implant extends from the cavity in the sleeve.

7. The packaging system of claim 6, wherein the flexible material film is vacuum formed over the sleeve to aid in stabilizing the sleeve and implant when inserted into an outer package.

8. The packaging system of claim 6, wherein the first side of the sleeve is not the same shape as the second side.

9. The packaging system of claim 6, wherein the first and second sides of the sleeve surround a second portion of the implant to protect the implant from surface abrasion during packaging, the surrounded portion of the implant being graspable via the sleeve so as to not contact the second portion of the implant.

10. The packaging system of claim 9, wherein the first portion of the implant is connectable to an insertion instrument while the implant is in the cavity of the sleeve.

* * * * *